(12) United States Patent
Sippel et al.

(10) Patent No.: US 7,348,151 B1
(45) Date of Patent: Mar. 25, 2008

(54) METHOD FOR THE CELLULAR HIGH-THROUGHPUT-DETECTION OF NUCLEAR RECEPTOR LIGAND INTERACTIONS

(75) Inventors: Albrecht E. Sippel, Freiburg (DE); André Zimmermann, Freiburg (DE)

(73) Assignee: Hansjoerg Forster, Eschwege (DE)

( * ) Notice: Subject to any disclaimer, the term of this patent is extended or adjusted under 35 U.S.C. 154(b) by 0 days.

(21) Appl. No.: 09/869,595

(22) PCT Filed: Dec. 29, 1999

(86) PCT No.: PCT/EP99/10461

§ 371 (c)(1),
(2), (4) Date: Jun. 7, 2002

(87) PCT Pub. No.: WO00/40717

PCT Pub. Date: Jul. 13, 2000

(30) Foreign Application Priority Data

Dec. 30, 1998 (DE) ................................ 198 60 834

(51) Int. Cl.
C70K 14/47 (2006.01)
C70K 14/72 (2006.01)
C70K 14/82 (2006.01)
C12N 15/62 (2006.01)
C12N 9/16 (2006.01)
C12N 33/566 (2006.01)
G01Q 1/68 (2006.01)

(52) U.S. Cl. ............................ 435/7.1; 435/7.2; 435/6; 435/69.1; 435/69.7; 435/254.2; 435/320.1; 436/501

(58) Field of Classification Search ................. 530/350
See application file for complete search history.

(56) References Cited

U.S. PATENT DOCUMENTS 5,443,962 A   8/1995  Draetta et al.

(Continued)

FOREIGN PATENT DOCUMENTS

WO   WO 94 28914 A   12/1994

OTHER PUBLICATIONS

Tissue Tropism, In, Medical Microbiology, S. Baron, Ed., 4th Edition, 1996.*

(Continued)

Primary Examiner—Manjunath Rao
Assistant Examiner—Daniel C Gamett
(74) Attorney, Agent, or Firm—Millen, White, Zelano, Branigan, P.C.

(57) ABSTRACT

The invention relates to fusion proteins comprising at least three domains, where
a first domain facilitates membrane localization of the fusion protein in a cellular context, and
a second domain has or presumably has a ligand-binding function of a nuclear receptor,
a third domain has an activity able to activate a signal pathway connected to a Ras protein in a cell, characterized in that when there is a lack of binding or, alternatively, when there is binding of ligand to the second domain the third domain cannot exert its activity to activate a signal pathway connected to a Ras protein in a cell, despite membrane localization. It additionally comprises inter alia cells which comprise such fusion proteins, assay methods using such cells, which are used inter alia for detecting specific interactions between ligand-binding sections of nuclear receptors and ligands, and kits for use in these assays.

38 Claims, 3 Drawing Sheets

Activation of the ras or of a ras-like signal transduction pathway
as a function of the interaction between nuclear receptor and its ligand in the absence of the ligand, the
ras or ras-like signal
transduction pathway is inactive in the presence of the ligand, the
ras or ras-like signal
transduction pathway is active

U.S. PATENT DOCUMENTS 5,776,689 A    7/1998 Elledge et al.

OTHER PUBLICATIONS

Mattioni et al., 1994, Methods in Cell Biology, vol. 43, Chapter 16.*
McMahon (2001, Methods in Enzymology vol. 332 pp. 401-417.*
The Cell: A Molecular Approach, 2nd Edition, 2000, by Geoffrey M. Cooper; figure 13.34.*
Thevelein et al., Molecular Microbiology vol. 33 pp. 904-918,Sep. 1999.*
Y.C. Broder et al., "The RAS Recruitment System, A Novel Approach to the Study of Protein-Protein Interactions," Current Biology, GB, Current Science, vol. 8. No. 20, pp. 1121-1124, Oct. 1998, XP000867036.
A. Aronheim et al., "CHP, A Homologue of the GTPASE CDC42HS, Activates the JNK Pathway And is Implicated in Reorganizing the Actin Cytoskeleton," Current Biology, GB, Current Science, vol. 8, No. 20, pp. 1125-1128. Oct. 1998, XP000867010.
A. Aronheim: "Improved Efficiency Sos Recruitment System: Expression of the Mammalian GAP Reduces Isolation of Ras GTPase False Positives," Nucleic Acids Research, vol. 25, No. 16, pp. 3373-3374, Aug. 15, 1997, XP002136255.
A. Aronheim et al., "Isolation of An AP-1 Repressor By A Novel Method for Detecting Protein-Protein Interactions." Molecular and Cellular Biology, US, American Society for Microbiology, Washington, vol. 17, No. 6, pp. 3094-3102, Jun. 1997, XP000867026.
A. Aronheim et al., "Membrane Targeting of The Nucleotide Exchange Factor SOS is Sufficient for Activating the RAS Signaling Pathway," CELL, US, Cell Press, Cambridge, NA, vol. 78, pp. 949-961, Sep. 23, 1994, XP002037807.
J. Schlessinger: "How Receptor Tyrosine Kinases Activate RAS," Trends in Biochemical Sciences, vol. 18, No. 8, pp. 273-275, Aug. 1993, XP002136256, Elsevier, Amsterdam, NL.

* cited by examiner

Figure 1:
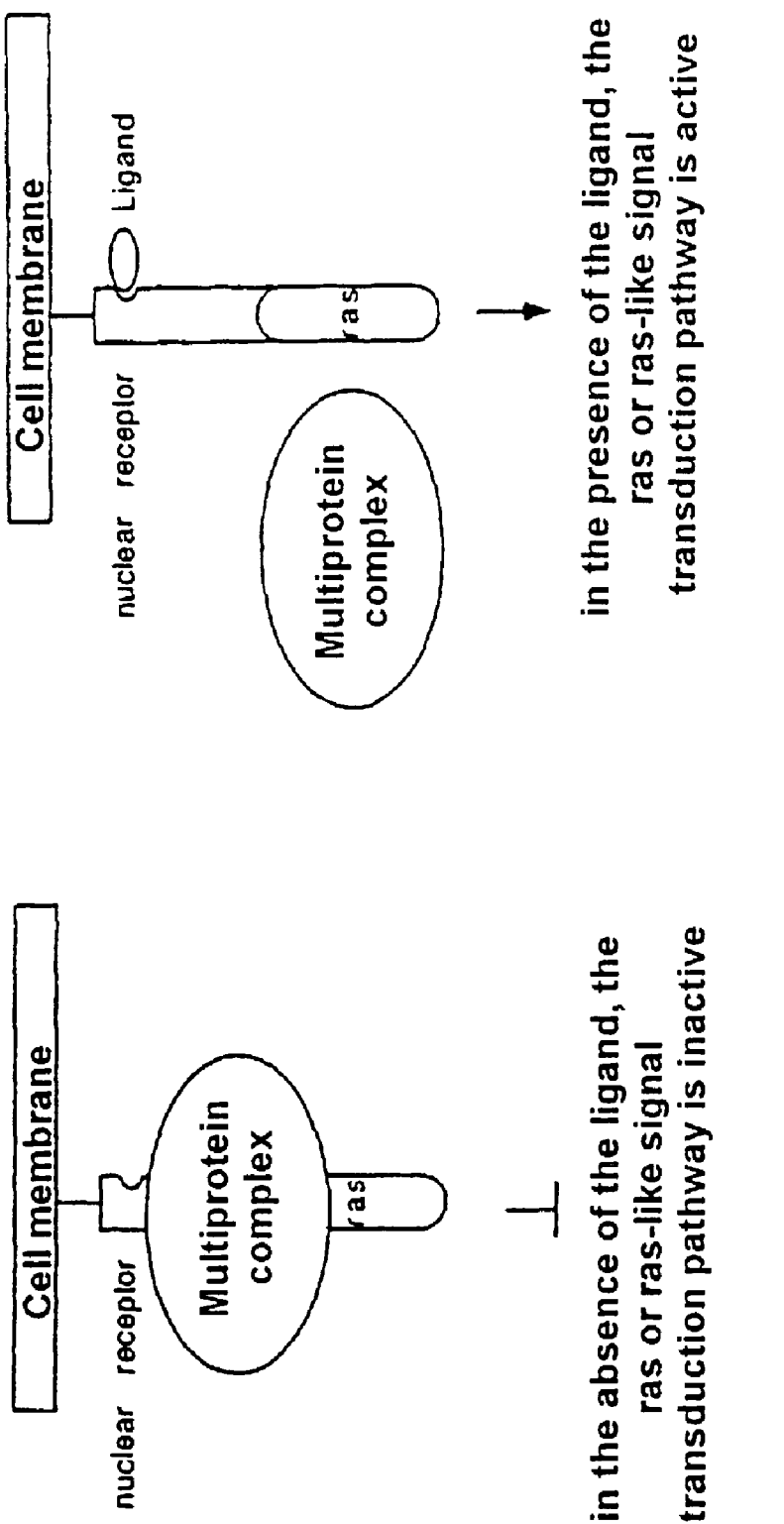

Fig. 1 Activation of the ras or of a ras-like signal transduction pathway as a function of the interaction between nuclear receptor and its ligand Diagrammatic representation of the structure of the membrane-localized estrogen receptor-ras fusion protein M : myristylation signal
LBD : ligand-binding domain of the human estrogen receptor (aa 282-595)
Ras : human ha-ras (L61) without CAAX box

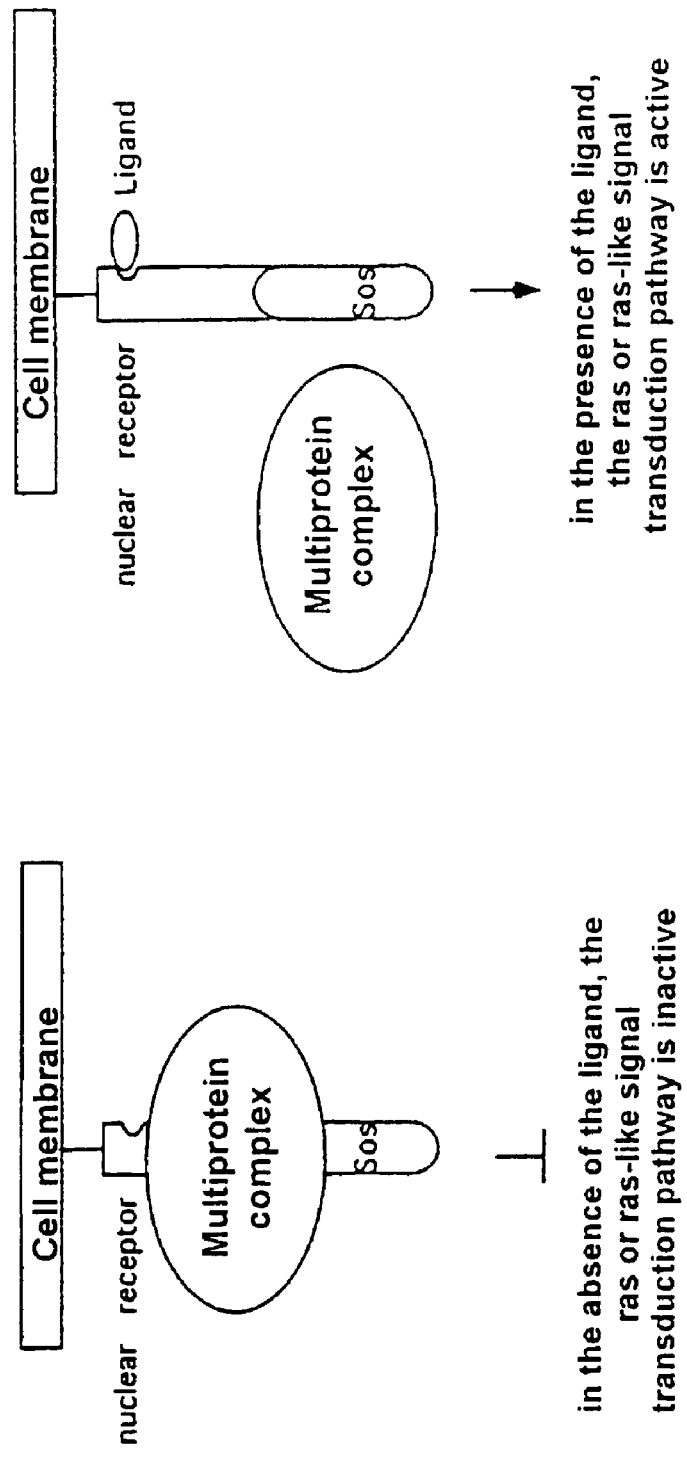

METHOD FOR THE CELLULAR HIGH-THROUGHPUT-DETECTION OF NUCLEAR RECEPTOR LIGAND INTERACTIONS

The invention relates to the area of molecular biology. It relates in particular to assay methods which are used to detect specific interactions between a ligand and a nuclear receptor, and aims inter alia at finding novel functional ligands for nuclear receptors and, where appropriate, detecting a ligand-binding function which is characteristic of nuclear receptors, in polypeptides or proteins suspected of such a function. In this connection, the invention also relates to fusion proteins, nucleic acids which encode these fusion proteins, vectors which comprise these nucleic acids, cells which comprise these fusion proteins, kits, all of which can be employed for the assay methods of the invention or in connection with the latter, and ligands for a binding section of a receptor, compounds able to alter a binding activity of a ligand-binding section of a receptor in relation to a ligand, and polypeptides or proteins which have a ligand-binding function of a receptor, all of which can be obtained or identified by the methods of the invention and, in particular, the assay methods of the invention.

The family of nuclear receptors differs from other receptor families (e.g. the 7-transmembrane receptor family or the tyrosine kinase receptor family) owing to the fact that they have neither a transmembrane domain nor any other type of membrane-localization or -anchoring signal. Without a bound ligand, they are present in inactive form either in the cytoplasm and/or in the cell nucleus. It is common to all members of this receptor family that, on binding of their ligand, they undergo a conformational change and are thus converted into a so-called "active" or otherwise effective form. The family of nuclear receptors includes, inter alia, the steroid receptors (Evans, Science, 240:889-95, 1988), the orphan receptors (Bargmann, Cell, 90: 585-587, 1997), the vitamin D receptor, the thyroxine, receptor, the dioxin receptor, the retinoic acid receptors and many other receptors (Kastner et al., Cell, 83: 859-869, 1995). Nuclear receptors play an important part in a large number of very diverse biological processes such as, for example, in the development of organisms, cell differentiation, cell division, gene regulation and, especially, also in the development of cancer (Seed, Nature Medicine, 4: 1004-1005, 1998).

Many medical therapies make use of the possibility of intervening, with the aid of certain pharmaceuticals, in processes controlled by nuclear receptors. The pharmaceuticals used in these cases act as agonists or antagonists of a naturally occurring ligand which is specific for a particular nuclear receptor.

For this and other reasons, there is great interest in being able to detect and study receptor-ligand interactions at the molecular level.

Several methods for detecting nuclear receptor-ligand interactions already exist. Most of these methods make use of the fact, for detecting such an interaction, that the receptor complexed with the ligand is able specifically to bind to DNA and to activate or to inactivate a so-called reporter gene in cells (U.S. Pat. Nos. 4,981,784 and 5,643,720). The disadvantage of such methods derives, inter alia, from the detection, which is complicated in some cases, of the reporter gene activity or the complexity associated with the manipulation of the vertebrate cells used.

In another approach, the receptor-ligand interaction is detected ex vivo, i.e. outside a living system, with either the receptor or the ligand being attached to a matrix and having flowing over it a solution containing the ligand or receptor. In this case, too, the effort for obtaining and attaching each individual receptor or ligand to the appropriate matrix surface is extremely great. Moreover, a problem arises in this connection in the extrapolation of the results obtained to the conditions in the cell, because the cellular conditions may differ considerably from the ex vivo conditions. A further serious problem is especially the lack of possibility of access to the genetic information of the novel receptor variants detected in screens or high-throughput assays.

The object on which the invention is based is to provide alternative assays suitable for detecting in vivo specific interactions between a ligand and a nuclear receptor, which have, inter alia, the advantages of being able to detect ligand-receptor interactions more quickly than possible in the prior art, and being capable of being carried out using cells which are simple to manipulate, such as prokaryotic cells or yeast cells. In addition, because of the design of the assay, there is always a direct possibility of access to the genetic information underlying a receptor variant.

Further objects of the invention comprise the provision of fusion proteins, nucleic acids, vectors, cells and kits, all of which can be employed for the assay methods of the invention or in conjunction with the latter, and ligands for a binding section of a receptor, compounds able to alter a binding activity of a ligand-binding section of a receptor in relation to a ligand, and polypeptides or proteins which have a ligand-binding function of a receptor, all of which can be obtained or identified using the methods of the invention and, in particular, the assay methods of the invention.

The objects on which the invention is based are met by the methods, in particular assay methods, fusion proteins, nucleic acids, vectors, cells, kits, ligands, compounds, polypeptides and proteins defined inter alia in the claims.

The present invention is based on the following realisations:

1. The activity of a protein able to activate a signal pathway connected to a Ras protein in a cell can be controlled by fusion to a nuclear receptor and/or parts of such as a function of the ligand binding to the receptor or receptor portion.

2. Activation of various ras signal transduction pathways requires membrane localization of certain components of the signal pathways (Schlessinger, TIBS, 18: 273-275, 1993). If these components are fused to a nuclear receptor and/or to parts of such, as explained under 1, it is possible on additional attachment of a further domain which facilitates membrane localization of the fusion product to create in a cell a system with which the activity of the component for activating the ras signal transduction pathway can be effective specifically at the site of action, i.e. on the membrane, only in the presence or, alternatively, only in the absence of a ligand for the nuclear receptor.

3. Cells in which a ras signal transduction pathway can be inactivated, at least under certain conditions, at the level of the Ras protein specific therefor or of a guanine nucleotide exchange factor specific for the Ras protein are known in the prior art. Insertion of the infusion protein which is explained above under 2. and which has a ras activity able to activate said ras signal transduction pathway into such a cell results in a cell in which the ras signal transduction pathway which is intrinsic to the cell and is inactive at least under certain conditions can be activated by the activity of the appropriately active component of the fusion protein—although only in the presence or, alternatively, in the absence of a ligand for the nuclear receptor section.

This results in a cell in which the or a particular ras signal transduction pathway can be activated only as a function of a ligand binding i.e. when ligand binding has taken place, or, alternatively, when there is a lack of ligand binding, to the nuclear receptor section of the fusion protein explained above. This cell makes it possible to establish an in vivo assay method which, on the basis of detecting an activation, which has taken place where appropriate, of the specific ras signal transduction pathway, where appropriate indirectly via specific effects detectable on or in the cell, such as cell growth, makes it possible to detect interactions between a nuclear receptor and a ligand specific therefor.

It may be added, for clearer understanding of the teaching of these documents, that the term "ligand" is intended to mean in the present context only those binding partners for receptors and, in particular, nuclear receptors which elicit on binding to the ligand-binding section or receptor section of such a receptor a conformational change which puts the third domain in the position of or, alternatively, prevents it from exerting its activity for activation of a signal pathway connected to a Ras protein in a cell. When the ligand dissociates off the ligand-binding or receptor section, i.e. when there is a lack of ligand binding, the third domain is, in the first variant mentioned above, accordingly not in a position to exert its activity for activation of a signal pathway connected to a Ras protein in a cell. In the second variant, the third domain has the ability to activate the signal pathway connected to a Ras protein in a cell only in the latter case. This may comprise, in particular, conformational changes like those taking place in vivo on binding of a natural ligand. In the case of nuclear receptors as already explained hereinbefore, the conformational change on ligand binding brings about, as mentioned, an activation and, in particular, probably, as is suspected on the basis of obtainable evidence, through dissociation off of a multiprotein complex which is brought about by the conformational change and which is present when ligand binding is lacking in firm association with the receptor.

However, cases in which the conformational changes do not correspond, or correspond only partly, to the conformational changes taking place on binding of a ligand occurring in vivo in the cell are also considered.

The meaning of the term "nuclear receptor" in the present context is moreover additionally also intended to extend to, for example, viral (including retroviral) non-membrane-associated receptors which likewise have the properties of being in inactive form without bound ligand but undergoing a conformational change on binding of their ligand and thus being converted into a so-called "active" form. It is moreover essential in connection with this variant of the invention that on integration of the ligand-binding domain of such a viral receptor into a fusion protein of the invention, and when there is a lack of ligand binding, the third domain cannot exert its activity to activate a signal pathway connected to a Ras protein in a cell, despite membrane localization; i.e. the activity of the third domain to activate a signal pathway connected to a Ras protein necessarily requires in this variant the binding of a ligand to the ligand-binding section derived from the viral receptor.

Alternatively, the possibility is provided, also in the case of viral receptors, that such receptors are in inactive form without bound ligand but undergo a conformational change on binding of their ligand and are thus converted into a so-called "active" form. In the context of the invention it is possible in this variant for the third domain, on integration of the ligand-binding domain of a corresponding viral receptor into a fusion protein of the invention and on the binding of ligand, not to exert its activity to activate a signal pathway connected to a Ras protein in a cell, despite membrane localization; this activity requires the ligand to dissociate off, that is to say a form of the fusion protein without bound ligand.

Thus, for the purposes of the invention and, in particular, in the case of viral receptors, besides the mechanism explained above for "activation" of the third domain in the form of a conformational change leading to dissociation off of a multiprotein complex, also conceivable are other activation mechanisms which, however, will always be conditional on a conformational change brought about by the ligand binding or, alternatively, dissociation off of ligand within the fusion protein.

The terms "ras signal pathway" or "signal pathway connected to a Ras protein", used synonymously herein, also embrace the so-called ras-like signal pathways which are controlled by various other members of the Ras family. Among the members of the Ras family there are ones which, despite originating from different organisms, are able to activate one and the same signal transduction pathway in the chosen target cell. One example thereof is the human Ha-Ras (L61) which is able also to activate a ras signal pathway in *Saccharomyces cerevisiae* which acts on the cell cycle and whose activation is essential for reproduction of yeast cells. Other members of the Ras family are able only to activate a single signal pathway specific for them.

A number of members of the Ras family, such as the aforementioned Ha-Ras (L61), activates signal pathways which act on the cell cycle and whose activation are essential for cell reproduction via activation of specific transcription factors. Other Ras proteins of this type activate signal pathways which specifically lead to activation in each case of one of a multiplicity of transcription factors which are specific for genes other than those of the cell cycle. In the present context, a common feature of all ras signal pathways is that they require for their activation an active Ras protein present on the cell membrane, and the Ras protein requires for its activity where appropriate the simultaneous presence of a guanine nucleotide exchange factor on the cell membrane.

Reference in these documents to an inactivation of a ras signal pathway or of a ras-like signal pathway always means an inactivation at the level of the ras protein and/or of a guanine nucleotide exchange factor specific therefor. Said signal pathway inactivation occurs in a cell in the present context preferably only under certain environmental conditions, such as temperature, and can thus be induced and abolished again by specific adjustment of environmental conditions.

An essential precondition of the assay systems of the invention is, as explained, the expression of a fusion protein with defined properties in a suitable cell system. As also depicted diagrammatically in FIGS. 1 and 3, this fusion protein, which likewise represents part of the invention, comprises domains or sections which confer on the fusion protein the following three functions or, in the case of the second function mentioned below, are intended to confer:

1. membrane localization, e.g. through a membrane-localization signal, a transmembrane domain and/or any other protein portion which facilitates membrane localization, 2. ligand-binding function of a nuclear receptor, e.g. through the provision of the sequence of a complete nuclear receptor and/or parts of one such, 3. ability to activate a ras or ras-like signal transduction pathway.

A further essential feature is that when there is a lack of binding or, alternatively, on binding of ligand to the second domain with ligand-binding function, the third domain cannot exert its activity to activate a signal pathway connected to a Ras protein in a cell, despite localization on the cell membrane. This activity requires the presence of a ligand bound to the second domain in the first variant mentioned above, and the dissociation off of ligand bound to the second domain in the last variant mentioned.

It is assumed, on the basis of the evidence briefly mentioned above and explained in detail hereinafter from various experiments on nuclear receptors that, in a preferred embodiment, when there is a lack of binding of ligand to the second domain the third domain with the activation function can be complexed by a multiprotein complex becoming attached to the fusion protein in such a way that the latter domain is unable to exert its activity to activate a ras or ras-like signal transduction pathway in a cell. An analogous mechanism is also conceivable as one possibility for the other variant, i.e. complexation and thus inactivation of the third domain when there is, however, ligand binding, with in this case the dissociation off of the ligand leading to a dissociation off of the multiprotein complex and thus the third domain being put into the position of exerting its activity to activate a signal pathway connected to a Ras protein.

As a result of various experiments on nuclear receptors, it is assumed that they are present in the cell without bound ligand as inactive multiprotein complex (Pratt, Endocr. Rev., 18: 306-60, 1997), which may consist of so-called heat shock proteins (HSPs) which are expressed in the cell. It is assumed that the attachment of the multiprotein complex takes place with a naturally occurring nuclear receptor in the vicinity, where appropriate the direct vicinity, of the ligand-binding site or else, where appropriate, in a region overlapping therewith. However, if it is intended to use the assay of the invention to examine the ligand-binding function of a mutated or artificially generated ligand-binding section, it may be necessary where appropriate additionally to provide one or more sections of nuclear receptors which are known or can be demonstrated to facilitate multiprotein complex binding but which no longer have a ligand-binding function. In this case, the second domain can be provided as chimeric sequence of amino acid sequences of varying origin. An alternative possibility, however, is for this additional sequence section also to be provided as another, fourth, domain in suitable arrangement within the fusion protein.

The additional provision of such an additional sequence section may also be considered in the case of ligand-binding sections derived from viral receptors if it is possible for a ligand binding to the ligand-binding section to bring about a conformational change such that a multiprotein complex (also) previously bound via the additional sequence section dissociates off.

However, the scope of the invention is also intended expressly to include alternative mechanisms for activation of the third domain resulting from ligand binding or, alternatively, because of lack of ligand binding because of a conformational change caused thereby.

The first function mentioned above has the effect that the fusion protein reaches the membrane and thus the site of action of that part of the fusion protein which is responsible for the third function. Implementation of the third function depends directly on the ligand-binding function, which is mentioned second, of the fusion protein and, in particular, on the presence of a ligand which interacts with this domain.

As mentioned, it is assumed that nuclear receptors are present in the cell in the absence of ligand as inactive multiprotein complexes. It is intended in a preferred embodiment that the same apply to the fusion protein of the invention, which contains in its second domain the sequence of such a nuclear receptor or of sections of one such. The multiprotein complex may in this case comprise in particular heat shock proteins (hsp) intrinsic to the cell. In this embodiment, multiprotein complex binding in the cellular context in the absence of ligand is an essential feature also in a fusion protein of the invention with a second domain which contains a mutated or artificial ligand-binding section, which has been designed, for example, by molecular modeling and has only a presumed ligand-binding function. It is necessary where appropriate for this purpose to provide within the fusion protein, as explained, an additional protein section which facilitates multiprotein complex binding in the absence of ligand, e.g. from a nuclear receptor. In both cases, this multiprotein complex prevents the activity of the third domain or, synonymously, ras or ras-like signal transduction component. However, if a specific ligand binds to the relevant nuclear receptor section, the multiprotein complex dissociates off from the receptor domain, as with nuclear receptors found. in vivo, and the ras or ras-like signal transduction component becomes active (see FIG. 1 and FIG. 3).

In the cellular context, a ras or ras-like signal transduction pathway is activated by the action of the active signal transduction components. On use of a cell in which this ras or ras-like signal pathway is not activated in the absence of the fusion protein because of mutations, at least under certain conditions, it is possible to detect such an activation mediated solely by the fusion protein via phenotypical changes, e.g. growth or gene or reporter gene activity, in the cell.

In preferred embodiments of this invention, the membrane-localization domain comprises the amino acid sequence of a farnesylation signal, myristylation signal or prenylation signal or is derived therefrom for example by amino acid exchange, modification, insertion or deletion.

In the region of the membrane-localization domain or as an additional sequence section which is, in particular, located at the N terminus it is also possible to provide a signal sequence which, although it does not serve to anchor the membrane receptor in the membrane as such, has the effect that the membrane receptor is transported after expression thereof with higher efficiency onto the cell membrane. The higher concentration, resulting therefrom, of membrane receptor in the immediate vicinity of the membrane results in a higher rate of incorporation of the membrane receptor into the cell membrane because of the membrane-localization domain. Such signal sequences are preferably used specifically suited to the cell type in which the membrane receptor is to be expressed because, for example, signal sequences effective in yeast are effective only with lower efficiency in mammalian cells, and vice versa. Examples of such signal sequences are signal sequences of GPCRs (G-protein-coupled receptors) intrinsic to yeast or of invertase intrinsic to yeast (SUC2) for preferred use in membrane receptors which are to be expressed in yeast cells.

The amino acid sequence of the second domain with ligand-binding function of a nuclear receptor may comprise the amino acid sequence of a naturally occurring nuclear receptor such as a steroid receptor, orphan receptor, vitamin receptor, for example vitamin D receptor, thyroxine receptor or retinoic acid receptor, or being derived therefrom, e.g. by amino acid attachment, exchange, modification, insertion or deletion. An alternative possibility is for the second domain to comprise a non-naturally occurring, synthetic receptor section, for example generated by molecular modeling, with where appropriate initially only suspected ligand-binding function.

The third domain is preferably able to activate ras signal transduction pathways which act on the cell cycle and whose activation is essential for cell reproduction. Alternatively and likewise preferably it acts on one of the Ras signal pathways which serves to activate transcription factors for genes which need not be essential for cell reproduction.

The third domain may have the activity of an active and, in particular, of a constitutively active Ras protein. Constitutively active Ras proteins show activity irrespective of the presence of guanine nucleotide exchange factor molecules, which various other Ras proteins require for their activity. For this purpose, the third domain may comprise, for example, the amino acid sequence of an active or constitutively active Ras protein which occurs in nature, e.g. the human Ha-Ras (L61), or of parts thereof. Or it may comprise amino acid sequences which are derived from such sequences, for example by attachment, exchange, modification, insertion or deletion of amino acids.

An alternative possibility is for the third domain to have the activity of a functional guanine nucleotide exchange factor. In this respect, the amino acid sequence of the third domain may likewise comprise, for example, sequences of naturally occurring guanine nucleotide exchange factors or partial sequences thereof, or it may be derived therefrom, for example by attachment, exchange, modification, insertion or deletion of amino acids. In a preferred embodiment, the amino acid sequence of the third domain is derived from the amino acid sequence of the CDC25 protein from *Saccharomyces cerevisiae*, of an SOS protein from a mammal or of an SOS-like protein derived from any organism.

In a preferred embodiment of this invention, which is illustrated diagrammatically in FIGS. 1 and 3, the individual domains are arranged within the fusion protein in the direction from the N terminus to the C terminus in the sequence first domain (membrane localization domain), second domain (domain with ligand-binding function), third domain (ras or ras-like signal transduction component). The arrangement of the individual domains may, however, also be otherwise. An example which may be mentioned here is a sequence from the N terminus toward the C terminus of third domain, second domain, first domain in succession.

It is possible, where appropriate, for the fusion protein of the invention also to comprise other domains or protein sections with or without function, as long as the functions explained above remain unimpaired or essentially unimpaired thereby.

In addition, the invention comprises DNA molecules which encode the fusion proteins of the invention, and vectors, in particular plasmids, cosmids, viral or phage genomes, which comprise at least one of these DNA molecules. Particular vectors of the invention are suitable for the transformation or transfection of host cells or for the expression of at least one fusion protein of the invention. For the latter purpose, a DNA molecule of the invention in the vector is under the control of a promoter which is capable of functioning in a host cell and which makes expression possible and controls it.

Preparation of the Fusion Proteins, DNA Molecules and vectors of the invention can take place by protocols known in the prior art (see, for example, Sambrook, J., Fritsch, E. F., Maniatis, T. (1989), Molecular Cloning. A Laboratory Handbook, Cold Spring Harbor Laboratory, New York; Current Protocols in Molecular Biology (1991)). Even if the fusion proteins can in principle be prepared by complete synthesis from individual amino acid derivatives, for which various methods are available in the prior art, they are normally produced by expression of the appropriate genes in cells. In this case, the gene for the fusion protein may be present extrachromasomally or integrated into the genome of the host cell. The cloning of the genes for the fusion proteins starting from known gene sections which encode protein sections with the necessary functions or else, in the case of the ligand-binding or receptor section, at present only presumed functions likewise form as part of the standard abilities of a skilled worker, such as the construction of vectors, such as transcription or transfection vectors or else expression vectors, in which the gene is present functionally linked to a promoter effective in the producing cell, the transformation or transfection of host cells as well as the cultivation of the transformed or transfected host cells for producing the protein. The isolation and purification of the fusion proteins of the invention can take place through use of conventional methods such as precipitation, use of various chromatographic methods such as gel filtration, affinity chromatography etc. Affinity chromatography in particular allows selective binding only of the fusion protein, for example on use of specific antibodies which are bound to the matrix and which are directed against a determinant of a section, which is heterologous in relation to the host cell, of the fusion protein. An alternative possibility is for the fusion protein to be expressed, for example, also as precursor protein which has an additional domain with a specific property of binding to a particular affinity column. After binding and subsequent elution from the affinity column it is then possible for the additional domain to be eliminated selectively from the precursor protein, which is now already in essentially pure form, to produce the fusion protein of the invention. However, where the additional domain has no effect on the suitability of the fusion protein for the assay of the invention, it is also possible alternatively to dispense with the elimination step. One example of such a domain consists of a plurality of, for example 10, histidine residues additionally attached at the N terminus ("His tag") and specifically binding to a metal chelate affinity chromatography column. Concerning all the techniques mentioned and the reagents necessary therefor, including vector molecules, reference may be made to standard literature (e.g. Sambrook, J., Fritsch, E. F., Maniatis, T. (1989), loc. cit.; Current Protocols in Molecular Biology (1991)) and an immense number of individual protocols.

Another central aspect of the invention are cells which comprise one or more of the fusion proteins of the invention. Within the framework of this invention it is moreover possible for single, a plurality of or else all domains of the fusion protein and/or where appropriate also parts of one or more domains to be heterologous in relation to the host or initial cell.

Because of the membrane-localization domain present in the fusion protein, the fusion protein is present membrane-bound in the cells. In this way, the second and third domains of the fusion protein are located intracellularly in the immediate vicinity of the cell membrane.

To prepare the cells of the invention it is possible, for example, to transform or transfect initial cells with an expression vector which contains a gene for the fusion protein of the invention under control of a promoter capable of functioning in the initial cell. Suitable initial cells are prokaryotic such as eukaryotic cells. Examples of initial cells are, inter alia, bacterial cells, such as those of the genus

*Escherichia* or *Bacillus*, for example certain strains of *Escherichia coli* or *Bacillus subtilis*, yeast cells, such as certain strains *Saccharomyces cerevisiae*, insect cells, animal cells such as COS-7, vero, CHO cells, mouse myeloma cells, human FL cells etc.

After transformation or transfection of an initial cell, the gene for the fusion protein of the invention may be present in the chromosome, that is to say integrated in the chromosome, or as constituent of an episome, in particular plasmid, i.e. extrachromosomally, in the transformed or transfected cell. The same applies to an additional transformation or transfection of cells also with other genes, in particular reporter genes or constructs with, as explained in detail hereinafter, is carried out in particular embodiments of the invention.

An essential feature of the cells of the invention is that, when there is a lack of binding or, alternatively, when there is binding of ligand to the second domain of the fusion protein, the third domain is not able to bring about activation of the signal pathway connected to a Ras protein in the cells.

In a preferred embodiment, the third domain is, when there is a lack of binding of ligand to the second domain, complexed by a multiprotein complex which becomes attached to the fusion protein and is preferably intrinsic to the cell, in such a way that the third domain is unable to bring about the activation of the signal pathway connected to a Ras protein in the cells. However, when a ligand binds to the second domain there is a conformational change with effects on the third domain, so that as a result the multiprotein complex dissociates off at least partly from the fusion protein, and the third domain can exert its activity to activate a signal pathway connected to a Ras protein in the cells.

In a preferred embodiment of this invention, the cell of the invention is characterized in that, in the absence of fusion protein, at least under certain conditions a signal pathway connected to a Ras protein cannot be activated in the cell and, in particular, the signal pathway which the third domain is able to activate. Thus, cells in which a particular ras signal transduction pathway is active or inactive depending on the temperature are known in the prior art. Cells of this type can be employed as initial cells for expression of the fusion protein of the invention.

The inactivation, which is present at least under certain conditions, of a ras signal transduction pathway results from a Ras protein and/or guanine nucleotide exchange vector which is incapable of functioning at least under the particular conditions. The inactivation may derive from genetic mutation or complete or partial gene deletion. For example, a Ras protein intrinsic to a cell can be inactivated when its membrane-localization signal, usually a farnesylation signal, is deleted. A mutation in this membrane-localization signal with the effect that binding of the Ras protein to the cellular membranes can no longer take place would have the same effect. One example of a cell with a temperature-dependently defective guanine nucleotide exchange factor is the *Saccharomyces cerevisiae* yeast strain cdc25-2. In this strain the guanine nucleotide exchange factor is no longer active at a restrictive temperature of 33 to 37° C., typically 36° C., but is fully capable of functioning at a temperature of, for example, 25° C. Since the guanine nucleotide exchange factor cooperates in this yeast strain with a Ras protein which controls a ras signal transduction pathway which acts on the cell cycle and is therefore essential for cell growth, no reproduction of the cells of the yeast strain is detectable at a restrictive temperature.

In a manner analogous to yeast strains with a temperature-sensitive mutation of an SOS protein intrinsic to yeast (CDC25-2) it is also possible to employ a yeast strain with a temperature-sensitive mutation of a Ras protein intrinsic to yeast.

An alternative possibility for preparing the cells of the invention is, however, also to use a cell, i.e. yeast cell or mammalian cell, which is in fact able to express a wild-type or mutated but active CDC25/SOS protein or Ras protein, but in which the gene encoding this active CDC25/SOS protein or Ras protein is under the control of an inducible promoter through which expression of the gene can be switched on or off deliberately by choosing particular culturing conditions. Examples of inducible promoters which can be employed in this connection are the galactose promoter or parts thereof from yeast or other organisms. The skilled worker is aware of a large number of inducible promoters suitable for this purpose from a wide variety of organisms. It is also possible to employ hybrid promoters with suitable inducibility.

If the cell of the invention expresses an active CDC25/SOS protein or an active Ras protein, it is possible in another preferred embodiment of the invention for the CDC25/SOS or Ras protein additionally to contain a modification through which the protein degradation in the cell is speeded up. This modification may be, for example, a ubiquitin signal or another signal which ensures the preferred degradation of a protein modified in this way in the cell. The advantage of expressing a protein modified in this way during induction of the promoter is that degradation of the CDC25/SOS or Ras protein produced at the time of induction of the promoter is speeded up after "switching off" of the promoter, i.e. after providing culturing conditions with which the promoter is not induced and accordingly there is no longer any transcription of the CDC25/SOS or Ras gene. Accordingly, even a short time after "switching off" of the promoter it is no longer possible to detect any such active CDC25/SOS or Ras protein in the cell. In the preferred situation where the third domain of the fusion protein of the invention is able precisely to activate the signal pathway which is activated by the active CDC25/SOS or Ras protein mentioned above, it is thus possible even a short time after changing the culturing conditions to switch off the promoter for the activation of this signal pathway to be measured exclusively on the basis of the effects of the fusion protein of the invention, which may signify a considerable advantage in terms of time. It is additionally possible in this way to reduce significantly the background signal based on an activation, which is possibly still present to a small extent and is not attributable to the fusion protein of the invention, of the signal pathway.

If the inactivation or inactivatability of the ras signal transduction pathway intrinsic to the cell is based on a defect or absence of a guanine nucleotide exchange factor, it is possible in the preferred case where the fusion protein has a third domain which is able to activate precisely this ras signal transduction pathway for this third domain to have the activity of a functional guanine nucleotide exchange factor or of an active, in particular constitutively active, Ras protein, each of which is able to activate the inactive ras signal transduction pathway. If a third domain with an activity of a non-constitutively active Ras protein is employed, it is reasonable for it to have the following properties:

it requires activation by a different type of guanine nucleotide exchange factor which is unable to interact functionally with the Ras protein, intrinsic to the cell, of the inactive ras signal transduction pathway. It is possible where appropriate for this specifically suitable guanine nucleotide exchange factor to be coexpressed as heterologous factor in the cell of the invention.

If the inactivation or inactivatability of the ras signal pathway intrinsic to the cell is attributable to a defect or absence of a Ras protein intrinsic to the cell, then in the preferred case where the fusion protein has a third domain which is able to activate precisely this ras signal pathway this third domain will have the activity of an active, in particular constitutively active, Ras protein. If the third domain has the activity of a non-constitutively active Ras protein, then activation thereof preferably takes place through a guanine nucleotide exchange factor intrinsic to the cell, but, as an alternative to this, it may also require a heterologous guanine nucleotide exchange factor to be coexpressed in the cell.

The techniques of molecular biology necessary for preparing the cells of the invention, e.g. cloning, vector construction, transformation or transfection, selection of transformed or transfected cells and calculation of the transformed or transfected cells etc., are well known to the skilled worker, and many general protocols exist for these purposes and may where appropriate require slight adaptation, see, for example, Sambrook, J., Fritsch, E. F., Maniatis, T. (1989), loc. cit.; Current Protocols in Molecular Biology (1991) and numerous protocols specifically drawn up for a particular cell type. The expression of the fusion protein may moreover, as mentioned, take place starting from a gene present extrachromosomally within an episome, for example plasmid, and take place starting from a gene integrated into the genome of the initial cell. Various techniques are available to the skilled worker for producing cells in which a particular ras signal transduction pathway is inactivated at the level of the Ras protein or of a guanine nucleotide exchange factor for specific gene inactivation, for example through antisense strategies or for targeted introduction of mutations or deletions in the particular genes or relevant genome sections. In particular, there are various known possibilities for preparing cell mutants in which transcription of the genes for example for the Ras protein or a guanine nucleotide exchange factor can be inactivated deliberately under certain conditions, e.g. temperature-dependently. For this purpose, these cells contain these genes in particular linked to promoters which become inactive under certain conditions, such as starting at a particular temperature.

In a particular embodiment of the invention, the cells of the invention are applied to a solid carrier. Suitable carrier substances known in the prior art are, in particular, polysaccharides, e.g. agarose, specific plastics such as polyacrylamides, polystyrene, polyvinyl alcohol, silicones, or else certain types of glass. The carrier may in this case be in the form of separate particles, for example beads, or of an essentially plate-like substrate, e.g. in the form of a microtiter plate. The covering of the carrier with the cells may be complete, as is usually the case for example with carrier beads, or else present on only parts or sections thereof, such as, for example only in the wells of a microtiter plate. In a preferred embodiment, the cells of the invention are immobilized on so-called biochips. Methods for immobilizing the cells on these carriers are known to the skilled worker. It is possible, depending on the chosen carrier type, for the cells to bind to the carrier without further measures. In this case, the solid carrier phase is incubated with an essentially homogeneous population of cells, resulting in adhesion thereof to the solid phase. An alternative possibility is for the immobilization also to take place for example by means of chemical reagents such as glutaraldehyde, formalin etc. Measures of these types are known to the skilled worker.

The fusion proteins and cells of the invention and cells which comprise these fusion proteins are the basis for a plurality of in vivo assay methods, to which this invention likewise relates. The assay methods which are explained in detail hereinafter can, on use of the first variant, i.e. when the third domain has activity only when there is ligand binding to the ligand-binding section (second domain) of the fusion protein of the invention, be used inter alia 1. to determine the suitability of a test substance as ligand for a nuclear receptor and, in this case, in particular to carry out mass screens with ligand derivatives in order to test which derivatives are able to bind to a ligand-binding section of a wild-type nuclear receptor,
2. to detect the presence of a particular ligand in a sample,
3. to determine the concentration of such a ligand in a sample,
4. to detect whether a compound is able to alter a binding activity of a ligand-binding section of a nuclear receptor in relation to a ligand, that is to say to act as agonist, antagonist or inhibitor, and in this case in particular to carry out mass screens for finding such agonistic or antagonistic compounds; and
5. to detect the ligand-binding function of a polypeptide or protein suspected of having such a function for ligands of nuclear receptors; the polypeptides or proteins may also be, in particular, novel nuclear receptors which are derived from natural receptors by mutation and whose ligand-binding function still needs confirmation; in this connection it is possible in particular to carry out mass screens with such novel, mutated ligand-binding sections which [lacuna] for example in the form of a receptor mutant library which contains, in particular, receptor mutants with randomly localized mutations in the ligand-binding section, in order to find novel artificial, functional ligand-receptor partners.

A first assay is used to determine the suitability of a test substance as ligand for a receptor section or, synonymously, ligand-binding section of a nuclear receptor and comprises the following steps:

(a) contacting the test substance with cells of the invention under conditions with which a signal pathway connected to a Ras protein cannot be activated in the cells in the absence of the fusion protein, where the fusion protein present in the cells contains a second domain comprising said receptor section, and a third domain which is able to activate the inactive signal pathway connected to a Ras protein, (b) investigating whether activation of the signal pathway connected to a Ras protein has taken place. Detection of the activation of the signal pathway connected to a Ras protein indicates in this case the ability of the test substance to bind to the second domain of the fusion protein and thus to the receptor section.

Another in vivo assay makes it possible to detect the presence of a ligand for a receptor section of a nuclear receptor in a sample which possibly contains the latter, and is characterized by the following steps:

(a) contacting the sample with cells of the invention under conditions with which a signal pathway connected to a Ras protein cannot be activated in the cells in the absence of the fusion protein, where the fusion protein present in the cells contains a second domain comprising said receptor section, and a third domain which is able to activate the inactive signal pathway connected to a Ras protein, (b) investigating whether activation of the signal pathway connected to a Ras protein has taken place.

In analogy to the former assay, detection of the activation of the signal pathway connected to a Ras protein indicates the presence of a ligand for the second domain of the fusion protein and, accordingly, for the receptor section of a nuclear receptor in the sample.

Preferred ras signal pathways are regarded in this connection as being, as explained, signal pathways which act on the cell cycle and whose activation is essential for cell reproduction. Alternative and equally preferred ras signal pathways serve to activate transcription factors for genes which need not be essential for cell reproduction.

Detection of ras signal pathway activation preferably takes place in the assays of the invention indirectly, i.e. via phenotypical changes, in this case in particular cell reproduction or gene or reporter gene activity, in the cells.

If, accordingly, the cells employed for the assays are ones in which the inactive signal pathway connected to a Ras protein is a signal pathway which acts on the cell cycle and whose activation is essential for cell reproduction, the steps (b) explained above comprise investigating whether the cells are capable of reproduction under the conditions mentioned, detection of the ability of the cells to reproduce indicates the ability of the test substance to bind to or the presence of a ligand for the second domain of the fusion protein and, accordingly, the receptor section of a nuclear receptor in the sample.

If, alternatively, the cells employed for the assays are those in which the inactive signal pathway connected to a Ras protein is a signal pathway which acts on the activity of a transcription factor for a gene which is not necessarily essential for cell reproduction, it is possible in the simultaneous presence of a construct comprising a binding site for the transcription factor, a minimal promoter cooperating therewith and a reporter gene under the control of the minimal promoter and heterologous in relation to the assay cell to use detection of expression of the heterologous reporter gene for establishing the activation of the ras signal transduction pathway and thus that ligand binding to the second domain has taken place. This is because only on activation of the ras signal transduction pathway is it possible for there to be activation of said transcription factor, which is subsequently able to activate, via binding to its binding site, the minimal promoter and thus makes expression of the reporter gene possible.

It is essential in this embodiment that the reporter gene and/or the reporter protein encoded thereby is a gene or protein which is heterologous in relation to the assay cell and whose presence can be specifically detected only when expression of the synthetic promoter-reporter gene construct takes place because of activation of the specific ras signal pathway and the resulting activation of the specific transcription factor. If detection takes place not via a direct detection of the transcription or translation product by means of nucleic acid probes or antibodies specific therefor, but takes place, for example, via the enzymatic activity of a translation product, it is necessary on use of enzyme-encoding genes to ensure beforehand that the assay cell used does not, before the transformation or transfection with the synthetic promoter-reporter gene construct, contain an enzymatic activity like that of the heterologous enzyme expressed on ligand binding. A corresponding statement applies to the other types of reporter protein.

An alternative possibility is also to employ a gene which is homologous in relation to the assay as reporter gene. Reporter gene expression as a result of a transcription factor activation which takes place only because of the activation, to be detected in the assay, of a signal pathway connected to a Ras protein in the cells will in this case lead to an increase in the amounts of reporter gene transcription product present in the cells and, where appropriate, also an increased amount of the report gene translation product, and these can be measured by means of comparative experiments without use of ligands, e.g. by Northern blotting or Western blotting.

If these two latter alternatives are chosen, it is necessary to know the particular transcription factor activated by the chosen ras signal transduction pathway, and the promoter section, or its sequence, cooperating with this transcription factor. In order to make this assay variant possible, the assay cell will be transformed or transfected with a construct comprising the promoter functionally linked to the reporter gene, which can, where appropriate, take place by cotransformation or cotransfection together with the construct which contains the gene encoding the fusion protein. As mentioned, these constructs may, after transformation or transfection of an initial cell, be present chromosomally or extrachromosomally, i.e. as constituent of an episome, e.g. plasmid, in the assay cell.

At present, a number of ras signal transduction pathways, e.g. in different eukaryotic organisms, have already been completely researched in relation to the transcription factors activated thereby and the promoter regions cooperating therewith. A number of possibilities is thus available to the skilled worker for a selection in this regard.

In a preferred embodiment of the invention, the reporter protein comprises a modification which results in faster breakdown or degradation of the protein in the cell. This modification may be, for example, a ubiquitin signal or other signal which ensures breakdown of a protein modified in this way. The advantage of the use of a reporter protein which is broken down faster in an assay cell is obvious in the light of fact that a low background expression of the reporter gene construct will virtually always be detectable under the assay conditions, even without activation of the signal pathway connected to a Ras protein through the fusion protein in the assay cell: the fast breakdown of the reporter protein significantly reduces the signal resulting from this background expression on detection of the protein level, i.e. of the reporter protein, because there is no accumulation of reporter protein over time. If, however, expression of the reporter protein is specifically activated by ligand binding to the fusion protein and, resulting therefrom, activation of a signal pathway connected to a Ras protein, unambiguous detection is possible because the background signal is low. Since the half-life of the reporter protein in the assay cell will always be sufficiently long, detection of the reporter protein, produced as a result of ligand binding to the fusion protein, will not be impaired in any way through the fast breakdown thereof.

The molecular biology techniques necessary for the preparation of transformation or expression vectors which contain the reporter gene functionally linked to a suitable specific promoter, and the transformation or transfection of cells, e.g. cloning, vector construction etc., are well known to the skilled worker and numerous general protocols exist therefor and require, where appropriate, at most slight adaptation (see, for example, Sambrook, J., Fritsch, E. F., Maniatis, T. (1989) loc. cit.; Current Protocols in Molecular Biology (1991)). The addition or fusion to a reporter gene of a sequence section which encodes a signal section which brings about faster breakdown of the expressed reporter protein, e.g. a ubiquitin signal, is well within the capacity of a skilled worker.

The skilled worker is aware of numerous genes which can be employed as reporter genes in this connection and which encode proteins which are amenable to simple and rapid detection. Examples thereof are genes which encode enzymatically active proteins, e.g. β-galactosidase, fluorescent proteins, e.g. GFP (green fluorescence protein) or chemiluminescent proteins. Another possibility comprises genes which encode proteins which can be detected using specific antibodies. In this case, the antibody carries a detectable label or can in turn be detected by a secondary, labeled antibody. Possibilities of these types are well known in the prior art. As already explained above, besides the necessity for detectability, it is essential only that the event to be detected in the cell, e.g. enzymatic activity, antibody binding, fluorescence, chemoluminescence, is undetectable in the absence of the construct with the gene for the reporter protein.

An alternative possibility is for the transcription of the reporter gene to be detected on the basis of the mRNA formed, by Northern blotting using probes specific therefor.

Another in vivo assay permits quantitative determination of the concentration of a ligand for the receptor section of a nuclear receptor in a sample which contains the latter, and comprises the following steps:

(a) contacting an aliquot of the sample with cells of the invention under conditions with which, in the absence of the fusion protein a signal pathway connected to a Ras protein in the cell cannot be activated, where the fusion protein present in the cells contains a second domain comprising said receptor section, and a third domain which is able to activate the inactive signal pathway connected to a Ras protein, (b) detecting quantitatively the extent of the activation of the signal pathway connected to a Ras protein by direct or indirect means, and (c) measuring the concentration of the ligand in the sample by comparing the measured extent of activation with corresponding values measured for known standard concentrations of the ligand.

If cells for which the ras signal transduction pathway which is inactive at least under certain conditions is a signal pathway which acts on the cell cycle and whose activation is essential for cell reproduction are used for quantitative detection of step (b), this takes place in a simple manner by determining the reproduction of the cells at a fixed time or the rate of reproduction of the cells under said conditions. The resulting data are then compared with data obtained on the basis of standard preparations of known concentration, and the concentration of the sample is determined by calculation.

An alternative possibility in this case too is to detect quantitatively the extent of ras signal pathway activation on the basis of the extent of the expression of a reporter gene in the cell. As explained above, expression thereof is possible only because of the activation, brought about as a result of the activation of the signal pathway connected to a Ras protein, of a specific transcription factor. With this detection variant, the assay preferably takes place under conditions which preclude cell reproduction, for example by using the cdc25-2 yeast mutant at restrictive temperatures, so that the amount of transcription product of the reporter gene or the expressed amount of reporter protein at a particular time or, alternatively, the expression rate of this reporter gene based on the transcription or translation product of the latter can be determined with an essentially constant number of cells. However, the quantitative determination may also take place under proliferation conditions if, at the same time, the number of cells is determined continuously or at defined time intervals, and the values found for reporter gene expression are converted into values per unit value of the number of cells.

An alternative possibility in this case too is to employ detection via expression of a reporter gene homologous to the host cell, in which case the increase in reporter gene expression observable at any time compared with the expression level present in cells without activation of the ras signal pathway is used to determine the result.

Another alternative in vivo assay makes it possible to detect whether a compound is able to alter a binding activity of a receptor section of a nuclear receptor in relation to a ligand, that is to say to act as agonist, antagonist or inhibitor. This assay is characterized by the following steps:

(a) contacting the ligand in the presence of the compound with cells of the invention under conditions with which the compound can diffuse into the cells or it is produced by the cells, and with which in the absence of fusion protein a signal pathway connected to a Ras protein in the cells cannot be activated, where the fusion protein present in the cells contains a second domain comprising said receptor section, and a third domain which is able to activate the inactive signal pathway connected to a Ras protein in the cells, (b) investigating whether and, where appropriate, to what extent activation of the signal pathway connected to a Ras protein takes place, (c) comparing the result of the investigation in step (b) with a result of an investigation obtained when the assay is carried out in the absence of the compound.

In this case, an increased activation of the ras signal transduction pathway in the presence of the compound indicates an agonist function of this compound, whereas a reduced or, where appropriate, even completely absent activation indicates an antagonist or inhibitory function of the compound.

Step (a) may moreover comprise adding the compound before the ligand to the cells, it being possible where appropriate to preincubate the compound with the cells, adding the compound separately but at the same time as the ligand to the assay cells, or mixing the compound beforehand with the ligand and, where appropriate, carrying out a preincubation of the two compounds, and only then adding the mixture to the assay cells.

If the compound is added to the cells it must be ensured that the compound can also diffuse into the cells in order to interact with the fusion protein therein. If the compound is a peptide, polypeptide or protein, the compound can also be prepared by expressing a gene coding therefor inside the cell itself. For this purpose, the cells can be transformed or transfected with an expression vector which contains such a gene. The means and methods necessary for this are well known to the skilled worker.

If the compound to be tested for its agonistic or antagonistic effect is expressed in the assay cell, then the expression of the gene coding therefor preferably takes place under the control of a constitutively active promoter and with use of cells in which the ras signal transduction pathway is inactivated only under the specific assay conditions. Such a system makes it possible to preclude expression of the compound in the cell on its own causing changes which might falsify the result of the assay. To preclude this it is necessary to detect under nonrestrictive conditions and in the absence of ligand the activity of the ras signal transduction pathway intrinsic to the cell, which is inactivated under restrictive conditions. Under nonrestrictive conditions and in the absence of ligand the fusion protein is inactive, so that the detectable activation of the ras signal transduction pathway indicates that the expression product does not interfere with any component of the ras signal transduction pathway and, in particular, not with the Ras protein or guanine nucleotide exchange factor specific therefor. It is possible in this way to preclude, or minimize the probability, that the expression product interacts with the third domain instead of with the second domain, so that its ability to activate the ras signal transduction pathway is abolished.

A corresponding test of activation of the particular ras signal transduction pathway under nonrestrictive conditions, in the presence of the compound and in the absence of ligand is carried out analogously with a compound added to the assay cells from outside.

If the ras signal transduction pathway which can be inactivated under the assay conditions is one whose activation is essential for cell reproduction, simply the normal reproducibility of the cells is ensured under nonrestrictive conditions. If detection takes place by use of a reporter gene activity, it is necessary to detect this reporter gene activity under nonrestrictive conditions.

For the detection under the restrictive conditions of the assay in step (b) there is likewise the possibility, for example, of detecting the activation of the signal pathway connected to a Ras protein via the expression, which takes place where appropriate and only on the basis of the activation resulting from the activation of the signal pathway connected to a Ras protein, of a reporter gene heterologous to the cells. The detection of the extent of the activation of the signal pathway connected to a Ras protein which takes place on detection of this activation may comprise a quantitative determination in which the amount, present in the cells, of transcription or translation product (reporter protein) of the reporter gene is determined at a particular time or the reporter gene transcription rate or the reporter protein expression rate is determined under the conditions mentioned.

An alternative possibility is also only to analyze aliquots, i.e. equal volumes of the assay solutions which have been produced and treated identically, apart from the addition of the compound, preferably ensuring equal or essentially equal numbers of cells in these aliquots. In this case the level of reporter gene expression is not quantified absolutely, but only a relative comparison of the levels of expression in the two assays is made possible.

In the case where the comparison in step (c) reveals that stronger expression of the reporter gene occurs in the presence of the compound, the compound is to be assumed to have an agonistic effect, and in the case where the comparison in step (c) reveals that lower expression of the reporter gene occurs in the presence of the compound, the compound is to be assumed to have an antagonistic effect. Like the quantitative assay described above, this assay is also preferably carried out under conditions with which no reproduction of the cells occurs.

An alternative possibility is for the reporter gene employed for the detection also to be homologous to the assay cell, in which case the increase, observable in each instance, in the expression, i.e. transcription and/or translation, of the reporter gene compared with the level of expression present in cells without activation of the ras signal pathway is used to determine the result.

If the cells employed for the assay are ones in which the inactive signal pathway connected to a Ras protein is a signal pathway which acts on the cell cycle and whose activation is essential for cell reproduction, step (b) comprises investigating whether and, where appropriate, to what extent the cells are capable of reproduction under the conditions mentioned. In the case where the comparison in step (c) reveals that greater cell reproduction occurs in the presence of the compound, the conclusion is that the compound has an agonistic effect, and in the case where the comparison in step (c) reveals that less cell reproduction occurs in the presence of the compound, the conclusion is that the compound has an antagonistic effect.

Like all the assays within the scope of this invention, this assay is also suitable in particular for mass screening, in this case for compounds which are nuclear receptor agonists and antagonists.

An alternative possibility is for this assay also to be used as additional test for confirming the ligand-binding property of a novel, in particular synthetic, ligand-binding section or for confirming the suitability of a test substance as ligand for the ligand-binding section. If the ligand-binding section has a ligand-binding property or if suitability as ligand for the ligand-binding section is present, it should be observed on use of a known agonist for the ligand employed for the first detection of the ligand property, or for the ligand-binding section that there is increased activation of the Ras or Ras-like signal pathway, and on use of a known antagonist for the ligand or the ligand-binding section that there is in return a reduced activation of the Ras or Ras-like signal pathway.

A further alternative in vivo assay makes it possible to detect whether a polypeptide or protein suspected of a ligand-binding function of a nuclear receptor in fact has this function. This assay comprises the following steps:

(a) contacting cells of the invention with the ligand under conditions with which in the absence of the fusion protein a signal pathway connected to a Ras protein in the cells cannot be activated, where the fusion protein present in the cells contains a second domain comprising said receptor section, and a third domain which is able to activate the inactive signal pathway connected to a Ras protein, (b) investigating whether an activation of the signal pathway connected to a Ras protein has taken place.

Detection of the activation of the signal pathway connected to a Ras protein indicates that the second domain of the fusion protein and, accordingly, the polypeptide or protein to be investigated has a ligand-binding function of a nuclear receptor.

For example, the fusion protein present in the cells may comprise a second domain which contains a receptor section derived from a naturally occurring receptor section of a nuclear receptor by mutation.

As previously, it is possible to detect the activation of the ras signal transduction pathway on use of cells with which the ras signal transduction pathway which is inactivate at least under certain conditions is a signal pathway which acts on the cell cycle and whose activation is essential for cell reproduction, on the basis of cell reproduction which takes place where appropriate.

An alternative possibility is to detect the activation of the ras signal transduction pathway also on the basis of the expression, which can be detected where appropriate, of a reporter gene in the cells. As explained, if the reporter gene is heterologous, expression thereof takes place only on the basis of the activation, resulting from the activation of the signal pathway connected to a Ras protein, of a specific transcription factor. In the case of a homologous reporter gene the aim is to detect the increase in reporter gene expression, e.g. on the basis of larger amounts of transcription or translation product, compared with the expression level without activation of the specific Ras signal transduction pathway.

When activity of the third domain using the second variant, i.e. only when there is a lack of ligand binding to the ligand-binding section (second domain) of the fusion protein of the invention, assay methods of the invention can be used, inter alia, for 1. determining the suitability of a test substance as ligand for a nuclear receptor and, in this case, in particular carrying out mass screens with ligand derivatives in order to test which derivatives are able to bind to the ligand-binding section of a wild-type nuclear receptor,
2. detecting the presence of a particular ligand in a sample,
3. detecting whether a compound is able to change a binding activity of a ligand-binding section of a nuclear receptor in relation to a ligand, that is to say to act as agonist, antagonist or inhibitor, and in this case in particular carrying out mass screens for finding such agonistic or antagonistic compounds;
4. detecting the ligand-binding function of a polypeptide or protein suspected of having such a function for ligands of particular nuclear receptors; in this case too it is possible for the polypeptides or proteins in particular to be novel ligand-binding sections, derived from natural receptors by mutation, of receptors whose ligand-binding function is yet to be confirmed; in this connection, it is possible in particular to carry out mass screens with such novel mutated ligand-binding sections which [lacuna] for example in the form of a receptor mutant library which contains in particular receptor mutants with randomly localized mutations in the ligand-binding section, in order to find novel artificial, functional ligand-receptor partners.

The aforementioned assays can take place essentially analogously to the assay variants explained previously, using the first variant, but in this case the detection of the activation of the Ras or Ras-like signal pathway indicates the absence of a ligand for the ligand-binding section of the investigated fusion protein in the assay cell. The latter assays will accordingly usually comprise two detections, specifically one detection in the presence of (potential) ligand, in which case no activation of the Ras or Ras-like signal pathway will be detectable if the (potential) ligand has a ligand-binding property for the ligand-binding section (second domain) of the fusion protein of the invention, and another detection in the absence of the (potential) ligand, in which case such an activation will ordinarily be detected.

In the detection of whether a compound is able to alter a binding activity of a ligand-binding section of a nuclear receptor in relation to a ligand, that is to say to act as agonist, antagonist or inhibitor, the detection takes place in the simultaneous presence of ligand and compound, in particular via a) the activation, which is possibly in fact detectable if the compound has an antagonistic or inhibitory effect, of the Ras or Ras-like signal pathway, for example with subsequent determination of the ligand concentration necessary for complete inactivity of the Ras or Ras-like signal pathway, at a particular concentration of compound, or a determination of the dependence of the signal pathway activation on the concentration of compound at a particular ligand concentration; or b) the inactivity, which is complete even at a relatively low ligand concentration when the compound has an agonistic effect, of the Ras or Ras-like signal pathway; in this case too it is possible to determine the dependence of the complete inactivity of the Ras or Ras-like signal pathway on the concentration of the compound and/or of the ligand in particular.

In the detection of a ligand-binding function of a polypeptide or protein suspected of such a function for ligands of particular receptors, the detection of the ligand-binding function takes place analogously via the inactivity of the Ras or Ras-like signal pathway in the presence of ligand when this signal pathway is active in the absence of ligand.

Detection of nuclear receptor-ligand interactions by means of the assay methods, cells and fusion proteins of the invention is not confined to eukaryotic cells as in vivo test system but can alternatively also take place in prokaryotic cells.

Concerning the assay conditions, no particular general requirements are necessary. However, in the case of detection of cell reproduction taking place where appropriate, it can thus be taken that the medium used makes this possible in principle. Where it is possible to inactivate genes and/or promoters in the cells, as explained, by choosing particular assay conditions, and inactivation is also intended during the assay, these conditions such as, for example, a particular restrictive assay temperature, in the case of cdc25-2 cells for example 33-37° C., should be maintained during the assay. The chosen reaction medium should moreover not interact with the test compound or the ligand which are added to the medium in any way to impair the assay.

The ligands which can be investigated and determined in all the assay methods explained above are naturally occurring substances such as hormones, in particular steroid hormones, vitamins, e.g. vitamin D, thyroxine or retinoic acid, as well as substances which do not occur naturally, e.g. synthetic derivatives of natural ligands or poisons, such as dioxin. Since the ligands of nuclear receptors are mainly small molecules with lower relative molecular mass and mainly hydrophobic nature, they diffuse without further measures into the assay cells of the invention in order to enter into binding therein with the ligand-binding section, which has an intracellular localization directly on the cell membrane, of the fusion protein. If desired and/or necessary, however, the cells can be pretreated before the assay in a suitable way in order to make the outer cell membrane more permeable for the test compound or the ligand to pass through. One example thereof is the preparation of cell ghosts lacking cell walls by, for example, enzymatic treatment of cells, for example of yeast cells lacking cell walls. Cell ghosts of this type and those prepared in another way, and cells with a cell wall modified in another way to increase the permeability are also embraced by the term "cells" in the present context.

Should the ligands to be tested be peptides, polypeptides or proteins, the latter may also be expressed in the assay cell starting from the nucleic acid constructs which encode the latter and have been introduced into the assay cell, in a special variant also non-constitutively but under the control of an inducible promoter; it is moreover possible for the constructs to be present in the assay cell after introduction into said cell chromosomally or extrachromosomally, i.e. as constituent of an episome, e.g. plasmid. The contacting of the assay cell with the ligand accordingly takes place in the case of non-constitutive expression under conditions with which expression of the ligand to be tested is induced in the cell. The skilled worker is aware of a large number of inducible promoters for this purpose, which can be induced, for example, by particular temperatures or chemical compounds.

It should in general be stressed that on addition of the ligand to be tested to the assay cell from outside constitutive expression is possible in the assay cell of all the components cooperating in the assay system of the invention, i.e. in particular the fusion protein and all the components of the signal pathway which is specifically activated by the third domain of the fusion protein and is connected to a Ras protein, which are involved only in this specific signal pathway. On expression of the ligand to be tested in the assay cell it is possible in the first variant, in which the third domain exerts its activity to activate a signal pathway connected to a Ras protein only on binding of ligand to the ligand-binding section of the investigated fusion protein, for all components of the assay system, now including the ligand, apart from one to be constitutively expressed in the assay cell. The assay system component(s) whose gene(s) is or are provided under the control of an inducible promoter is or are then expressed in particular only under assay conditions, i.e. on investigation of the possible activation of the Ras or Ras-like signal transduction pathway, on the basis of the specific induction of the inducible promoter or promoters employed in each case. In the second variant, in which the third domain of the fusion protein can exert its activity only when there is a lack of ligand binding to the second domain of the fusion protein, on expression of the ligand in the assay cell its gene will always be provided under the control of an inducible promoter in order to make detection possible even in the absence of the ligand.

Detection of the activation of the ras signal transduction pathway takes place in a manner familiar to the skilled worker depending on the detection strategy. If the cells are immobilized on a solid carrier during the assay, it may be necessary or helpful, in particular in the case of detection of a reporter gene activity or transcription or of a reporter protein, to solubilize the cells before the detection reaction, i.e. to detach them from the carrier and, where appropriate, also disintegrate them. The measures and reagents necessary for this purpose are also well known to the skilled worker.

The invention additionally provides kits for use in the assays of the invention, which make it possible, for example, to determine rapidly and efficiently whether a specific ligand is able to bind to a particular nuclear receptor or parts of such receptors.

A first kit of the invention for use in the assaying methods for determining the suitability of a test substance as ligand for a receptor section of a nuclear receptor, for determining the presence of a ligand for a receptor section of a nuclear receptor in a sample, for determining the concentration of such a ligand, and for characterizing compounds as possible agonists or antagonists in relation to nuclear receptor-ligand interactions comprises in each case cells of the invention with the properties explained above in detail for the assay methods. Thus, the cells in the kit contain, for example when it is intended to detect a reporter gene activity, additionally a construct with a binding site for the transcription factor which is activated specifically through the ras signal pathway whose activation is to be detected by the assay, with a minimal promoter and with the reporter gene. An alternative possibility is for the kit as well as all following ones to comprise a transformation or transfection vector which contains the construct. It is possible in this way for the user of the kit on choice of this detection route to equip the assay cells present in the kit with this construct by transformation or transfection. In another embodiment of this and all following kits, the transformation or transfection vector provided separately in the kit contains only the binding site for the transcription factor and the minimal promoter functionally linked thereto, and a suitably provided insertion site for the insertion of a reporter gene which can be chosen freely by the user.

In addition, this kit, as well as all following ones, may contain inter alia where appropriate also an assay buffer, reagents for detecting the phenotypical activation of the signal transduction pathway connected to a Ras protein in these cells and/or instructions for use.

An alternative kit for the aforementioned assay methods comprises the following components:

a) cells in which at least under certain conditions the signal pathway connected to Ras protein cannot be activated, b) one or more transformation or transfection vectors which contain at least one DNA sequence which encodes the fusion protein as defined above, where the fusion protein comprises a third domain able to activate the inactive or inactivatable signal pathway connected to a Ras protein in the cells, c) where appropriate reagents for transformation or transfection of the cells with the transformation or transfection vector, d) where appropriate reagents for detecting the phenotypical activation of the signal transduction pathway connected to a Ras protein in these cells.

Another alternative kit makes it possible to prepare the assay cell with a fusion protein which contains an individually desired second domain. It comprises the following components:

a) cells in which at least under certain conditions a signal pathway connected to a Ras protein cannot be activated, b) a transformation or transfection vector which has, in suitable arrangement,
   a DNA sequence which encodes a first domain of a fusion protein as defined above,
   a DNA sequence which encodes a third domain of a fusion protein as defined above and which is able to activate the inactive or inactivatable signal pathway connected to a Ras protein in the cells, and
   a suitably arranged insertion site for functional insertion of a DNA sequence which encodes a second domain as defined above, where, after insertion of a DNA sequence for the second domain, the vector comprises a complete gene for a fusion protein as defined above, c) where appropriate reagents for transformation or transfection of the cells with the transformation or transfection vector, d) where appropriate reagents for detecting the phenotypical activation of the signal transduction pathway connected to a Ras protein in these cells.

It also applies to the two latter assays that the cells present in the kit may, for an intended detection of a reporter gene activity inter alia additionally also contain a construct comprising a binding site for a transcription factor whose activation results from the activation of the specific ras signal pathway whose activation is to be detected by the assay, a minimal promoter and the reporter gene as explained above, or it is possible alternatively to provide, separately from the cells, a transformation or transfection vector with the transcription factor binding site-minimal promoter-reporter gene construct or with another type of construct comprising the transcription factor binding site and the minimal promoter and, in addition, a suitably arranged insertion site for a reporter gene which can be chosen freely.

The invention also provides kits for the assay methods of the invention for detecting whether a polypeptide or protein has a ligand-binding function of a nuclear receptor. A kit suitable for this purpose comprises cells of the invention, and the fusion protein present therein comprises a second domain comprising a polypeptide or protein suspected of having a ligand-binding function of a nuclear receptor.

An alternative kit comprises the following components:

a) cells in which at least under certain conditions a signal pathway connected to a Ras protein cannot be activated, b) one or more transformation or transfection vectors which comprise at least one DNA sequence which encodes a fusion protein as defined above, whose second domain comprises a polypeptide or protein suspected of having a ligand-binding function of a nuclear receptor, and whose third domain is able to activate the inactive or inactivatable signal pathway connected to a Ras protein in the cells, c) where appropriate reagents for transformation or transfection of the cells with the transformation or transfection vector, d) where appropriate reagents for detecting the phenotypical activation of the signal transduction pathway connected to a Ras protein in these cells.

An alternative kit for use in said assay makes possible the specific provision of an assay cell with a fusion protein which comprises as second domain a desired polypeptide or protein which is to be investigated for its ligand-binding function. Such a kit comprises:

a) cells in which at least under certain conditions a signal pathway connected to a Ras protein cannot be activated, b) a transformation or transfection vector which has, in suitable arrangement, a DNA sequence which encodes a first domain of a fusion protein as defined above, and a DNA sequence which encodes a third domain of a fusion protein as defined above and which is able to activate the inactive or inactivatable signal pathway connected to a Ras protein in the cells, a suitably arranged insertion site for functional insertion of a DNA sequence which encodes a second domain containing a polypeptide or protein suspected of having a ligand-binding function of a nuclear receptor, where, after insertion of a DNA sequence for the second domain, the vector comprises a complete gene for a fusion protein as defined above, in which the second domain contains a polypeptide or protein suspected of having a ligand-binding function of a nuclear receptor, c) where appropriate reagents for transformation or transfection of the cells with the transformation or transfection vector, d) where appropriate reagents for detecting the phenotypical activation of the signal transduction pathway connected to a Ras protein in these cells.

If it is intended to detect a reporter gene activity, in one embodiment the cells in the aforementioned kits additionally contain a construct comprising a binding site for a transcription factor whose activation results from activation of the specific ras signal pathway whose activation is to be detected by the assay, a minimal promoter and the reporter gene, as explained above, or it is possible alternatively to provide, separately from the cells, a transformation or transfection vector with the transcription factor binding site-minimal promoter-reporter gene construct or with another type of construct comprising the transcription factor binding site and the minimal promoter and, in addition, a suitably arranged insertion site for a reporter gene which can be chosen freely.

In a preferred embodiment of the invention, the kits of the invention comprise the cells immobilized on a solid carrier, as explained above, in particular on biochips. Immobilization of the cells in the individual wells of microtiter plates is particularly suitable for mass screens, so that a plurality of separate assay methods can be carried out on such a plate. It is also possible in this connection to provide different cells of the invention, i.e. in particular cells with different second domain, in wells in respectively defined sections on one and the same microtiter plate.

If the cells in the kit are immobilized on a solid carrier it may be necessary or helpful, in particular on detection of a reporter gene activity or of a reporter protein, to solubilize the cells before the detection reaction, i.e. detach them from the carrier and, where appropriate, also disintegrate them. In this case it is possible for the reagents mentioned under d) for detecting the phenotypical activation of the ras signal transduction pathway also to comprise suitable solubilizing reagents which, in particular, contain one or more surface-active agents or surfactants.

In addition, the invention also extends to ligands for a binding section of a receptor, compounds which are able to alter a binding activity of a ligand-binding section of a receptor in relation to a ligand (referred to as "modifying compounds" hereinafter) and polypeptides or proteins having a ligand-binding function of a receptor, which have been determined or found by means of one of the assay methods of the invention, and compositions containing these ligands, compounds and/or polypeptides or proteins.

In relation to polypeptides or proteins having a ligand-binding function of a receptor and having been derived from a naturally found or synthetically produced molecule for production of the fusion protein comprising at least three domains, where a first domain mediates membrane localization of the fusion protein in a cellular context, a second domain has or presumably has a ligand-binding function of a nuclear receptor, a third domain has an activity able to activate a signal pathway connected to a Ras protein in a cell, characterized in that when there is a lack of binding or, alternatively, when there is binding of ligand to the second domain the third domain cannot exert its activity to activate a signal pathway connected to a Ras protein in a cell, despite membrane localization, the invention comprises both the fragment which is present in the fusion proteins employed according to the invention and has a ligand-binding function, and the initial fragment or molecule. It may be remarked in relation to this, only for the sake of clarity, that the production of the fusion protein usually takes place by expression of a nucleic acid sequence encoding this fusion protein in a cell. A polypeptide or protein with ligand-binding function of a receptor is accordingly derived from a larger initial molecule usually in an analogous way at the nucleic acid level, by merely using one or more sections of the nucleic acid sequence encoding the initial molecule, where appropriate with subsequent cloning for attachment of sections which encode other fusion protein components or sections, for expression of the fusion protein. The deriving may also include one or more slight nucleic acid sequence modifications in the initial sequence or in the nucleic acid section(s), preferably of a type such that the resulting nucleic acid molecule still hybridizes under stringent conditions with the respective initial nucleic acid molecule.

The invention accordingly also comprises a method for identifying polypeptides or proteins, in particular receptors, which have a ligand-binding function of a receptor, which comprises:

preparing a cell of the invention with a fusion protein comprising at least three domains, where a first domain mediates membrane localization of the fusion protein in a cellular context, a second domain has or presumably has a ligand binding function of a nuclear receptor, a third domain has an activity able to activate a signal pathway connected to a Ras protein in a cell characterized in that when there is a lack of binding or, alternatively, when there is binding of ligand to the second domain the third domain cannot exert its activity to activate a signal pathway connected to a Ras protein in a cell, despite membrane localization, and comprising the whole of such a polypeptide or protein or a part of such a polypeptide or protein which presumably contains the sequence sections essential for the ligand-binding function, and using this cell to carry out the in vivo assay method of the invention for detecting whether a polypeptide or protein has a ligand-binding function of a nuclear receptor, and the molecules identified by this method.

The invention likewise extends to the use of the aforementioned ligands, modifying compounds and polypeptides or proteins, identified by the assay methods of the invention, as pharmaceuticals, where appropriate after formulation with excipients and/or carriers customary in this sector, and the use of the ligands, modifying compounds and polypeptides or proteins as lead substances for developing ligands, modifying compounds and polypeptides or proteins which are derived therefrom—in particular by derivatization—in particular those with corresponding or improved activity compared with the respective lead substance.

Thus, the invention also comprises a method for preparing ligands, modifying compounds, polypeptides or proteins by derivatization one or more times starting from ligands, modifying compounds, polypeptides or proteins identified by the assay methods of the invention. This method may comprise, where appropriate, additionally the steps of also testing the ligands, modifying compounds, polypeptides or proteins obtained by the derivatization, using the assay methods of the invention, for ligand function or ligand-binding function and/or formulating the ligands, modifying compounds, polypeptides or proteins obtained by the derivatization, as pharmaceutical in conventional way.

The invention further extends also to the ligands, modifying compounds, polypeptides and proteins obtained by this method, i.e. the functional derivatives obtained by this method.

For a use as gene therapeutic agents intended to bring about the expression of a polypeptide or protein which has a ligand-binding function of a receptor, in particular nuclear receptor, in particular in human or animal cells, the invention further comprises nucleic acid molecules which are obtained, starting from a polypeptide or protein, in particular receptor, identified by the assay, identification, screening or preparation methods of the invention, by a method which comprises the provision of the gene encoding the polypeptide or protein, or a part, which comprises at least the nucleic acid sequence sections essential for the activity of the encoded polypeptide or protein, of this gene, in essentially pure form, i.e. in particular essentially free of other nucleic acids which are unnecessary or even deleterious for use as gene therapeutic agent. This method may, if not yet known, require preceding identification of the gene which encodes this polypeptide or protein. In particular, the method may additionally also comprise the following steps:

if not yet known, determination of the amino acid sequence of the polypeptide or protein, in particular receptor, and/or if not yet known, identification of the gene which encodes this polypeptide or protein, and determination at least of the sequence of the coding sections of this gene, where appropriate carrying out modifications in the resulting nucleic acid sequence, for example for adaptation of the codon usage to that of a desired recipient organism, for introducing mutations or deleting intron sequences, and formulation of the nucleic acid sequence which has been modified where appropriate in the form of a gene therapeutic agent.

In a currently preferably used experimental system of the invention, a mutated Ras protein (Ha-Ras (61L), which is a constituent of the fusion protein encoded by the nucleic acid sequence, lacks the farnesylation sequence ensuring a membrane localization of the protein. In addition, the yeast strain cdc25-2 is used as cell system which is inactive in a ras or ras-like signal transduction pathway. As explained, the Ras protein is non-functional in these cells at a restrictive temperature of 33-37° C.; typically 36° C., as a consequence of the absence of a functional guanine nucleotide exchange factor (GEF; "guanyl nucleotide exchange factor"). Expression of a functional, membrane-associated Ras protein fused to a nuclear receptor and/or parts of one such can be detected by the fact that the yeast cells are able to grow irrespective of the presence of a functional GEF protein at said restrictive temperatures if a suitable ligand of the expressed nuclear receptor is present.

In order to explain the invention further, an example is now described by way of example.

Material and Methods

Figure 2:

The basic vector used is a vector with a marker gene (Ura) and a galactose-inducible promoter (GAL1) for the fusion gene to be expressed. As shown diagrammatically in FIG. 2, the DNA sequence to be expressed encodes:

1. a myristylation signal,
2. the ligand-binding domain of the human estrogen receptor (amino acids 282-595),
3. the human Ha-Ras (L61) which is constitutively active and which lacks the so-called CAAX box, the farnesylation signal for membrane localization.

Yeast Growth and Manipulation

Conventional yeast transformation and manipulation protocols (see, for example, Hill et al. (1991), NAR 19, 5791) were used. The cells were plated out either on a glucose minimal medium which contains the necessary amino acids and nucleotides (20 mg/l histidine, 100 mg/l leucine, 20 mg/l tryptophan, 20 mg/l uracil, 10 mg/l adenine sulfate), 2% glucose, 0.5% $NH_4SC_4$, 0.17% yeast extract and 4% agar, or on galactose medium (1.7 g/l yeast nitrogen without amino acids, 5 g/l ammonium sulfate, 30 g/l galactose (>99%) 20 g/l D-raffinose, 20 g/l glycerol (100%), 30 g/l Bacto Agar).

Clones were plated out on YPD medium (1% yeast extract, 2% Bacto tryptone and 2% glucose) as control. YPD medium contains no galactose, so that there ought to be no expression of the fusion protein. Successfully transformed clones showed, as expected, no cell reproduction on cultivation on this medium with addition of the ligand estrogen.

Replica platings were carried out with velvet replica plater. After transformation with the nucleic acid vector described above, the cells were plated out on glucose plates and incubated at a non-restrictive temperature of 25° C. for three to four days. Various liquid media (with and without estrogen) were then inoculated with in each case 3 independent clones and incubated at 37° C. for 12 to 36 h, and then the growth of the yeasts in the various liquid media was detected by photometric measurement of the optical density at 600=m. The following table gives an overview of the media chosen and the response obtained.

TABLE 1

Detection of growth of cdc25-2-yeast cells as a function of various estrogen concentrations in the medium

| | Glu medium − E | Glu medium + E ($10^{-5}$M) | Gal medium − E | Gal medium+ + E ($10^{-6}$M) | Gal medium + E ($10^{-7}$M) | Gal medium + E ($10^{-8}$M) | Gal medium+ + E ($10^{-9}$M) | Gal medium + E ($10^{-10}$M) |
|---|---|---|---|---|---|---|---|---|
| 25° C. | + | + | + | + | + | + | + | + |
| 37° C. | − | − | − | + | + | + | +/− | − |

Glu medium: glucose medium
Gal medium: galactose medium
E: estrogen
−: no growth of the yeasts
+: growth of the yeasts
+/−: weak growth of the yeasts

REFERENCES

Bargmann, Cell, 90: 585-587, 1997;
Current Protocols in Molecular biology, 1991;
Evans, Science, 240: 889-895, 1988;
Hill, NAR, 19: 5791, 1991;
Kastner et al., Cell, 83: 859-869, 1995;
Pratt, Endocr. Rev., 18: 306-360, 1997;
Sambrook, J., Fritsch, E. F., Maniatis, T. (1989), Molecular Cloning. A Laboratory Handbook, Cold Spring Harbor Laboratory, New York;
Schlessinger, TIBS, 18: 273-275, 1993;
Seed, Nature Medicine, 4: 1004-1005, 1998.

We claim:

1. A fusion protein comprising at least three domains, wherein
   a first domain mediates a membrane localization of the fusion protein in a cellular context, wherein the signal of said membrane localization comprises an amino acid sequence which comprises a farnesylation signal or prenylation signal,
   a second domain has a ligand-binding function and comprises an amino acid sequence which comprises the receptor portion of a steroid receptor, and
   a third domain which comprises an amino sequence which comprises a Ras protein that is able to activate a signal pathway connected to a Ras protein in a cell, wherein when there is a lack of binding to the second domain of said fusion protein, the third domain cannot exert its activity to activate a signal pathway connected to a Ras protein in a cell, despite membrane localization, but when there is binding of ligand to the second domain of said fusion protein, said signalling pathway is activated.

2. A fusion protein as claimed in claim 1, wherein the individual domains are arranged within the fusion protein in the direction from the N terminus to the C terminus in the sequence first domain, second domain, third domain or in the sequence third domain, second domain, first domain.

3. A fusion protein as claimed in claim 1, wherein the third domain comprises a Ras protein which has guanine nucleotide exchange factor (GEF)-independent activity.

4. A DNA molecule which encodes the fusion protein as claimed in claim 1.

5. A vector comprising at least one DNA molecule as claimed in claim 4.

6. A vector as claim in claim 5, which is suitable for the transformation or transfection of a host cell.

7. A vector as claimed in claim 5, which is suitable for expression of at least one fusion protein, and comprises at least one DNA molecule as claimed in claim 5 under the control of one or more promoters capable of functioning in a host cell.

8. A eukaryotic cell comprising a fusion protein as claimed in claim 1, wherein when there is a lack of binding of ligand to the second domain of the fusion protein, the third domain is unable to exert its activity to activate a signal pathway connected to a Ras protein in the cell, despite membrane localization, but when there is binding of ligand to the second domain the third domain is able to exert its activity to activate a signal pathway connected to a Ras protein in the eukaryotic cell.

9. A eukaryotic cell as claimed in claim 8, which is a single-cell eukaryotic cell.

10. A eukaryotic cell as claimed in claim 8, wherein the intrinsic signal pathway connected to a Ras protein is inactivated in the eukaryotic cell.

11. A eukaryotic cell as claimed in claim 10, wherein the signal pathway connected to a Ras protein acts on the eukaryotic cell cycle and its activation is essential for cell reproduction or the signal pathway connected to a Ras protein alternatively serves to activate transcription factors for genes which are not essential for cell reproduction.

12. A eukaryotic cell as claimed in claim 10, wherein the intrinsic signal pathway connected to a Ras protein is inactivated in the eukaryotic cell by temperature treatment.

13. A eukaryotic cell as claimed in claim 12, wherein the lack of activatability of the signal pathway connected to Ras protein in the absence of fusion protein at particular temperatures is derived from at least one mutation of a guanine nucleotide exchange factor intrinsic to the eukaryotic cell, which has the effect that the latter is incapable of functioning above a particular temperature.

14. A eukaryotic cell as claimed in claim 13, which is a eukaryotic cell of the *Saccharomyces cerevisiae* yeast strain cdc25-2 or is derived from the latter.

15. A eukaryotic cell as claimed in claim 13, wherein the eukaryotic cell comprises a fusion protein whose third domain has the activity of a Ras protein that has guanine nucleotide exchange factor (GEF)-independent activity.

16. A eukaryotic cell as claimed in claim 12, wherein the lack of activatability of the signal pathway subsequent to a Ras protein in the absence of fusion protein at particular temperatures is derived from at least one mutation of a Ras protein intrinsic to the eukaryotic cell, which has the effect that the latter is incapable of functioning above a particular temperature.

17. A eukaryotic cell as claimed in claim 10, wherein the lack of activatability of the signal pathway connected to a Ras protein in the absence of fusion protein derives from a deletion of the membrane-localization signal, in particular farnesylation signal, of the Ras protein intrinsic to the eukaryotic cell or from a mutation of this membrane-localization signal which has the effect that the Ras protein no longer binds to cellular membranes.

18. A eukaryotic cell as claimed in claim 16, comprising a fusion protein whose third domain has the activity of a Ras protein that has guanine nucleotide exchange factor (GEF)-independent activity.

19. A eukaryotic cell as claimed in claim 8, which is applied to a solid carrier.

20. A eukaryotic cell as claimed in claim 19, which is immobilized on a biochip.

21. An in vivo assay for determining the suitability of a test substance as ligand for a receptor section of a steroid receptor, comprising:
  (a) contacting the test substance with cells as claimed in claim 10 under conditions with which a signal pathway connected to a Ras protein cannot be activated in the cells in the absence of the fusion protein, where the fusion protein present in the cells contains a second domain comprising said receptor section, and a third domain which, when there is binding of ligand to the second domain, is able to activate the inactive signal pathway connected to a Ras protein,
  (b) determining whether activation of the signal pathway connected to a Ras protein has taken place, where detection of the activation of the signal pathway connected to a Ras protein indicates the ability of the test substance to bind to the second domain of the fusion protein and thus to the receptor section.

22. An assay as claimed in claim 21, where step (b) comprises detecting the activation of the signal pathway connected to Ras protein via reporter gene expression which takes place optionally and only because of the activation, resulting from the activation of the signal pathway connected to a Ras protein, of a specific transcription factor, where detection of the expression of the reporter gene indicated the ability of the test substance to bind to the second domain of the fusion protein and, accordingly, to the receptor section.

23. An assay as claimed in claim 21, wherein the test substance is a hormone, a vitamin, thyroxine or retinoic acid.

24. An assay as claimed in claim 21, wherein the test substance is a non-naturally occurring substance.

25. An assay as claimed in claim 24, wherein the test substance is dioxin.

26. A screening method for unknown ligands of a steroid receptor, wherein an assay method as claimed in claim 21 is employed for the screening.

27. A kit for use in an assay or screening method comprising cells as claimed in claim 8.

28. A kit for use in an assay, comprising the following constituents:
  a) eukaryotic cells wherein the intrinsic signal pathway connected to a Ras protein is inactivated in said eukaryotic cell,
  b) one or more transformation or transfection vectors comprising at least one DNA sequence which encodes a fusion protein comprising
    a first domain mediates a membrane localization of the fusion protein in a cellular context, wherein the signal of said membrane localization comprises an amino acid sequence which comprises a farnesylation signal or prenylation signal,
    a second domain has a ligand-binding function and comprises an amino acid sequence which comprises the receptor portion of a steroid receptor, and
    a third domain which comprises an amino sequence which comprises a Ras protein that is able to activate a signal pathway connected to a Ras protein in a cell, wherein when there is a lack of binding to the second domain of said fusion protein, the third domain cannot exert its activity to activate a signal pathway connected to a Ras protein in a cell, despite membrane localization, but when there is binding of ligand to the second domain of said fusion protein, said signalling pathway is activated,
  c) optionally comprising reagents for transformation or transfection of the cells with the transformation or transfection vector,
  d) optionally comprising reagents for detecting the phenotypical activation of the signal pathway connected to a Ras protein in these cells.

29. A kit for use in an assay as claimed in claim 21, comprising the following constituents:
  a) eukaryotic cells wherein the intrinsic signal pathway connected to a Ras protein is inactivated in said eukaryotic cell,
  b) a transformation or transfection vector which has, in suitable arrangement,
  a DNA sequence which encodes a first domain of a fusion protein as defined in claim 21,
  a DNA sequence which encodes a third domain of a fusion protein as defined in claim 21 and which is able to activate the inactive or inactivatable signal pathway connected to a Ras protein in the cells when there is binding of ligand to the second domain, and
  a suitably arranged insertion site for functional insertion of a DNA sequence which encodes a second domain as defined in claim 21,
  where, after insertion of a DNA sequence for the second domain, the vector comprises a complete gene for a fusion protein as claimed in claim 21,
  c) optionally comprising reagents for transformation or transfection of the cells with the transformation or transfection vector,
  d) optionally comprising reagents for detecting the phenotypical activation of the signal transduction pathway connected to a Ras protein in these cells.

30. A kit as claimed in claim 27, in which the cells additionally contain a construct comprising a binding site for a transcription factor whose activation results from an activation of a specific ras signal pathway whose activation is to be detected by the assay, a minimal promoter and a reporter gene functionally linked thereto, where the minimal promoter is activated as a result of binding of the activated transcription factor to its binding site.

31. A kit as claimed in claim 27, additionally containing a transformation or transfection vector with a construct comprising a binding site for a transcription factor whose activation results from an activation of a specific ras signal pathway whose activation is to be detected by the assay, a minimal promoter and a reporter gene functionally linked thereto, where the minimal promoter is activated as a result of a binding of the activated transcription factor to its binding site.

32. A kit as claimed in claim 27, additionally containing a transformation or transfection vector with a construct comprising a binding site for a transcription factor whose activation results from an activation of a specific ras signal pathway whose activation is to be detected by the assay, a minimal promoter and an insertion site, suitably arranged for expression controlled by the minimal promoter, for insertion of a gene for a reporter protein, where the minimal promoter is activated as a result of a binding of the activated transcription factor to its binding site.

33. A kit as claimed in claim 27, which contains the cells immobilized on a solid carrier.

34. A cell as claimed in claim 9 which is a yeast cell.

35. A cell as claimed in claim 34 which is a yeast cell lacking cell walls.

36. A vector of claim 5 which is a plasmid, cosmid or viral or phage genome.

37. A kit of claim 33 wherein said solid carrier is a microtiter plate or a biochip.

38. An assay as claimed in claim 23, wherein the hormone is a steroid hormone.

* * * * *